(12) United States Patent
Lüchinger

(10) Patent No.: US 7,591,169 B2
(45) Date of Patent: *Sep. 22, 2009

(54) MEASURING INSTRUMENT FOR GRAVIMETRIC MOISTURE DETERMINATION

(75) Inventor: Paul Lüchinger, Uster (CH)

(73) Assignee: Mettler-Toledo AG, Greifensee (CH)

( * ) Notice: Subject to any disclaimer, the term of this patent is extended or adjusted under 35 U.S.C. 154(b) by 209 days.

This patent is subject to a terminal disclaimer.

(21) Appl. No.: 11/769,415

(22) Filed: Jun. 27, 2007

(65) Prior Publication Data

US 2008/0049809 A1    Feb. 28, 2008

(30) Foreign Application Priority Data

Jul. 7, 2006    (EP) ................................ 06116840

(51) Int. Cl.
*G01N 5/02* (2006.01)
(52) U.S. Cl. .................. 73/73; 73/75; 73/76; 374/14
(58) Field of Classification Search ................ 73/73, 73/75, 76; 374/14
See application file for complete search history.

(56) References Cited

U.S. PATENT DOCUMENTS

| 4,964,734 A | 10/1990 | Yoshida et al. |
| 5,485,684 A | 1/1996 | Philipp et al. |
| 6,920,781 B2* | 7/2005 | Olesen ............... 73/73 |
| 2004/0103718 A1* | 6/2004 | Olesen ............... 73/76 |
| 2007/0245813 A1* | 10/2007 | Luchinger ........... 73/76 |
| 2007/0256479 A1* | 11/2007 | Luchinger ........... 73/76 |
| 2008/0006082 A1* | 1/2008 | Luchinger ........... 73/73 |

FOREIGN PATENT DOCUMENTS

| DE | 3305846 A1 | 8/1984 |
| EP | 1148329 A1 | 10/2001 |
| FR | 2606510 A1 | 8/1988 |
| GB | 2202054 A | 9/1988 |

* cited by examiner

*Primary Examiner*—Andre J Allen
(74) *Attorney, Agent, or Firm*—Standley Law Group LLP

(57) ABSTRACT

A measuring instrument for gravimetric moisture determination of a sample includes a radiator, a weighing cell, and a sample receiver which can be connected to the weighing cell. The sample receiver is configured to allow the sample to be placed on or removed from the sample receiver. The radiator has a radiation-releasing surface directed at the sample and that covers substantially the entire surface of the sample with a uniform radiation intensity. The radiator is arranged above the sample, relative to the direction of the load, and spans over the entire sample. The measuring instrument also includes a means for removing the moisture emitted from the sample during the operation of the instrument device from the space between the sample and the radiation-releasing surface.

27 Claims, 4 Drawing Sheets

MEASURING INSTRUMENT FOR GRAVIMETRIC MOISTURE DETERMINATION

CROSS-REFERENCE TO RELATED APPLICATIONS

This application claims a right of priority under 35 USC §119 from European patent application 06116840, filed 7 Jul. 2006, the content of which is incorporated by reference as if fully recited herein.

TECHNICAL FIELD

The present invention relates to a measuring instrument for the gravimetric determination of moisture content.

BACKGROUND OF THE ART

To determine the moisture content in a sample, the sample is dried and the weight of the sample is measured before and after the drying process. Due to the extensive amount of work involved, this method is very expensive as well as error-prone.

In some cases, the weight loss can also be measured during the drying process. In a given sample, the decrease in weight is a function of the temperature, the length of the drying time, and the conditions in the test compartment, and it conforms to a weight-versus-time curve which asymptotically approaches the dry weight of the sample. The curve for the given sample is determined by comparative experiments and can be expressed mathematically through an approximation formula. A measuring instrument for gravimetric moisture determination which is appropriately equipped with available electronic technology can compute the moisture content of a sample based on the measured parameters of the aforementioned curve and based on the length of the drying time and indicate the result on a display unit. With this method, the substance to be dried does no longer need to be totally desiccated; it is sufficient to determine the coordinates of two measurement points in the weight-versus-time diagram.

As has already been mentioned at the beginning, the weight change of a sample is substantially a function of the temperature, the length of the drying time, and the conditions in the test compartment. Especially the stringent requirements imposed on the test compartment and its design features are setting a limit to the accuracy of the commercially available instruments.

The term "test compartment" in the present context means a space which is enclosed by the housing of the measuring instrument and which can be opened in order to insert or remove a sample. Also arranged inside the test compartment are a sample receiver and a means to heat the sample. The sample receiver is connected to a gravimetric measuring instrument.

Normally, the sample is spread in a thin layer onto a flat sample receiver, for example a sample tray. The tray is preferably arranged in the measuring instrument for gravimetric moisture determination in such a way that the sample-carrying area is horizontally leveled, so that samples of low viscosity cannot collect at the lowest point (relative to the direction of the load) of the sample tray.

As a means for heating the sample, a variety of radiation sources are used, such as heat radiators, microwave generators, halogen- and quartz lamps. A gravimetric moisture-determination instrument of the aforementioned type is disclosed in commonly-owned U.S. Pat. No. 5,485,684, issued 23 Jan. 1996 to Philipp, et al. In this instrument, the sample substance is put on the weighing pan while the latter is outside of the gravimetric moisture-determination instrument. To do this, the balance is pulled out of the housing of the measuring instrument on a sliding carrier like a drawer. For a radiation source, a ring-shaped halogen lamp is used which is located above the sample receiver when the instrument is in its operating condition.

As was found in experiments, the type and the design configuration of the radiation source being used are among the primary causes for inaccurate measurement results in existing gravimetric moisture-determination instruments. For example, radiators with perforations or radiators whose radiation originates substantially from a point or a line can cause a non-uniform irradiation of the sample with the result that the energy density in individual spots of the sample can be so high as to cause in some places a thermal breakdown of the sample.

If the radiator spans over the sample in a spread-out and largely flat configuration, it is possible that a moisture-saturated gas cushion will form between the sample and the radiator and remain in place, whereby a further escape of moisture from the sample is prevented. Such an obstruction to the drying process could have a significant effect on the drying time, wherein in particular the temperature-related random atmospheric convection between the radiator and the sample enter into the measuring result.

The errors in the drying time that are caused by the obstruction in the drying process, and/or the measurement errors in the sample weight values due to thermal decomposition impose a limit on the accuracy that can be obtained in an analysis with the aforementioned mathematical model. As an alternative to using the mathematical model, one can use the known method in which all of the moisture—to the extent that this is possible—has to be driven out of the sample. However, this requires a very long drying time, which increases the risk that a thermal decomposition or oxidation of the sample will occur as a result of the long, sustained exposure to the heat radiation of the radiators.

For the reasons that have just been explained, it is hardly possible to determine an absolute value for the moisture content with a gravimetric moisture-determination instrument. For a more accurate determination of the moisture content of a substance or for the calibration of dryers, the known Karl Fischer titration method is therefore still in use. This method is very labor-intensive, prone to user errors, and expensive.

It is therefore an object to provide a gravimetric moisture-determination instrument of the kind mentioned in the introduction with a radiator that has an improved distribution of the radiation over the sample. Furthermore, the escape of moisture from the sample should not be compromised as a result of the improved distribution of the radiation.

SUMMARY OF THE INVENTION

This objective is met with a measuring instrument for the gravimetric determination of moisture in accordance with the appended claims.

The measuring instrument for gravimetric moisture determination includes at least one radiator, a weighing cell, and a sample receiver which can be connected to the weighing cell. The sample receiver is of a configuration that allows a sample to be placed on or removed from the sample receiver. The at least one radiator has a radiation-releasing surface directed at the sample and covering substantially the entire surface of the sample with a uniform radiation intensity. Furthermore, the radiator is arranged above the sample, relative to the direction of the load, and spans over the entire sample. The measuring instrument contains a removing device which serves to remove the gaseous medium between the sample and the radiation-releasing surface which becomes enriched with moisture during operation of the instrument.

This removing device can be designed in very different ways.

In a first embodiment of the measuring instrument, at least the radiation-releasing surface of the at least one radiator is arranged to be rotatable relative to the sample. If during operation of the measuring instrument the moisture is driven out of the sample due to the exposure to radiation, in particular heat radiation, a moisture-saturated gas cushion can develop between the radiation-releasing surface and the sample. As the radiation-releasing surface of the radiator is set into rotation, parts of the gas cushion in the immediate vicinity of the radiation-releasing surface are dragged along and, as a result of the centrifugal force, are pushed out into the border area of the radiation-releasing surface. From there, the moisture-enriched medium that has been moved into the border area can be picked up and removed for example by the flow current of a suction device. As another possibility, the heated gaseous medium is displaced from the immediate vicinity of the sample receiver in the border area by an inflow of cold, and therefore heavy, gaseous medium. As a result, the warm, gaseous medium rises up in the test compartment and leaves the latter through ventilation slits, as known from the existing state of the art.

Thus, a radiation-releasing surface that is supported in a way that allows rotation serves as a removal device as soon as it is set into rotation. Of course, this includes the possibility of a rotatable support for the entire radiator so that it can be set into rotation. The rotation can be driven by an active or passive system. Active systems include for example an electric motor, while a passive system is represented for example by a turbine that is driven by the hot gaseous medium, for example air, which streams upward in the test compartment.

As explained above, the spinning radiation-releasing surface drags along parts of the gas cushion. The larger the surface roughness of the rotatable radiation-releasing surface, the more of the gaseous medium is moved out to the border area of the radiation-releasing surface at a given rate of rotation of the latter. The radiation-releasing surface therefore has a surface roughness that is preferably equal to or larger than 0.0001 mm. However, as the roughness increases, the uniformity of the radiation distribution over the radiation-releasing surface may decrease. But the concept whereby the radiation-releasing surface rotates relative to the surface of the sample has the additional benefit of supporting the objective of a uniform radiation distribution. Furthermore, the surface roughness also needs to be matched to the distance of the sample from the radiator. The shorter this distance, the finer the surface roughness that should advantageously be chosen, because the spinning radiation-releasing surface causes turbulent air drafts which can have a negative influence on the weighing result if they are too strong. In addition, the rate of rotation of the revolving radiation-releasing surface depends on the radiation intensity or on the temperature, as the escape of moisture from the sample is as a rule directly dependent on these quantities.

Because the rotation has a distributing effect, the radiation-releasing surface can also have at least one ridge, groove, depression or channel, without any major negative effect on the radiation distribution. There are hardly any constraints imposed on the configuration nor on the number of these ridges, grooves, depressions or channels on the radiation-releasing surface.

However, the raised areas of the ridges are preferably equal in their shape and size to the depressed areas formed between the ridges, so as not to compromise the radiation distribution between the center of rotation and the border of the radiation-releasing surface.

In a second embodiment of the measuring instrument, at least one static displacement body of radiation-transmitting material is arranged between the sample and the radiator and serves as removal device. This embodiment makes use of the effect that the heated gaseous medium is displaced from the space between the radiation-releasing surface and the sample and pushed towards the radiation-releasing surface by an inflow of cold and heavy gaseous medium. The requirement for providing the most uniform radiation distribution possible while keeping the cost down imposes strong constraints on the design possibilities for the radiation-releasing surface, as will be described in the following. Easiest to realize is a radiator with a planar radiation-releasing surface arranged parallel to the sample. However, this has the consequence that the moisture-saturated medium stagnates between the sample and the radiation-releasing surface. What enables the moisture-filled gases to be removed is the static displacement body, as the shape of the displacement body directs the heated gaseous medium to the border area of the radiation-releasing surface. It needs to be emphasized that the kind of convective flow that is caused purely by thermal factors and will necessarily occur between the radiation-releasing surface and the sample does not constitute a removal device as intended herein. Only in connection with the static displacement body are the thermal convection effects representing a removal device of the intended type.

To prevent the moisture absorbed by the gaseous medium from condensing on the surface of the static displacement body, the latter is ideally equipped with a partially absorbent member which convert a small part of the radiation into heat and thus heat up the entire static displacement body or the surface portion facing towards the sample. Such partially absorbent member can be for example a surface with a vapor-deposited metal film, metallic fillers in the material of the displacement body, metallic inserts, foils, screens, canvas and the like.

Depending on the design, the at least one static displacement body can be connected to the radiation-releasing surface or to a part of the housing of the measuring instrument.

As far as the shape of the static displacement body is concerned, there are hardly any limits, because due to its transparency to radiation the static displacement body has very little influence on the radiation distribution over the surface of the sample. The ideal choice for the static displacement body is a cone-shaped or hemispherical bonnet or a curved plate. The only concern in the design of the static displacement body is that the heated gaseous medium must not become trapped. When a planar plate is used, it needs to be set for example at an angle a relative to the load direction, so that in its upward rise, the heated gaseous medium is at least deflected to one side under a slope angle $\alpha$ which should be in the range $0°<\alpha<90°$.

In a third embodiment of the measuring instrument, the radiation-releasing surface and in some cases the static displacement body can have a rotary bearing at the center. A shaft that is rotatable about an axis parallel to the load direction can pass through this bearing, wherein at least one dynamic displacement body can be connected to the end of the shaft that faces towards the sample. The smaller the cross-sectional area of the bore hole and the shaft is in relation to the area of the radiation-releasing surface, the less it interferes with the radiation distribution. Ideally, the shaft itself emits radiation. Preferably, the radiation coming from the shaft is matched to the respective distances of the shaft and the radiation-releasing surface from the sample.

The dynamic displacement body can likewise have different configurations. It is for example conceivable to use a kind of wiper blade sweeping at a narrow distance over the radiation-releasing surface. As a further possibility, several wiper blades could be attached to the end of the shaft in a star-shaped arrangement. The wiper blades can furthermore be curved in the radial and/or axial direction relative to the axis of the shaft, similar to the blades of a turbine or pump wheel.

To improve the flow rate of the removal device, the radiation-releasing surface can spin with the opposite sense of rotation relative to the shaft with the at least one dynamic displacement body. This allows the rate of rotation of the radiation-releasing surface and the shaft in relation to the sample to be kept relatively slow, which can have a very positive effect on suppressing excessive turbulence in the space between the sample and the radiator.

However, the dynamic displacement body can also be configured as a cone-shaped or spherical bonnet and extend over the entire radiation-releasing surface, in which case the dynamic displacement body needs to be made of a radiation-transmitting material, analogous to the static displacement body.

As described above in connection with the static displacement body, the dynamic displacement body can be equipped at least in part with a partially absorbent member and/or with at least one ridge, groove, channel or depression.

It is also possible to use combinations of the embodiments described above. To perform the function of a removal device, at least the radiation-releasing surface of the at least one radiator can be arranged so that it can rotate relative to the sample, at least one dynamic displacement body can be connected to the radiation-releasing surface, and the radiation-releasing surface as well as the first dynamic displacement body, if applicable, can have a rotary bearing at the center. A shaft can pass through this bearing, constrained by the latter to rotate or swivel, wherein at least one second dynamic displacement body is connected to the end of the shaft that faces towards the sample, and wherein the first dynamic displacement body turns with the opposite sense of rotation relative to the second dynamic displacement body.

In order to achieve as uniform a radiation distribution as possible over the entire sample, the respective areas covered by projecting the radiation-releasing surface and the sample into a plane that is orthogonal to the load direction are preferably of identical size and shape.

This condition can be met in a simple way in particular if the radiation-releasing surface is arranged substantially parallel to the surface of the sample, if it is of a flat and planar configuration, with the radiator itself having a uniform radiation intensity over the entire radiation-releasing surface.

These requirements are met to an excellent degree for example by hot plates and by heating foils mounted on flat metal bodies. Local non-uniformities in the generation of heat are equalized within the metal body, so that the heat radiation is emitted with uniform intensity over the entire radiation-releasing surface.

The static or dynamic displacement body preferably covers the entire radiation-releasing surface, so that the latter is protected against contamination.

Ideally, the static displacement body is connected to the radiation source or to the housing through releasable fastening means, so that for the purpose of cleaning the displacement body can be taken out of the test compartment and subsequently installed again.

It is also practical if the at least one dynamic displacement body and/or the radiation-releasing surface are connected to the shaft through releasable fastening means.

BRIEF DESCRIPTION OF THE DRAWINGS

Details of the measuring device can be found in the following description of the embodiments illustrated in the drawings, wherein.

DETAILED DESCRIPTION OF A PREFERRED EMBODIMENT

Figure 1:
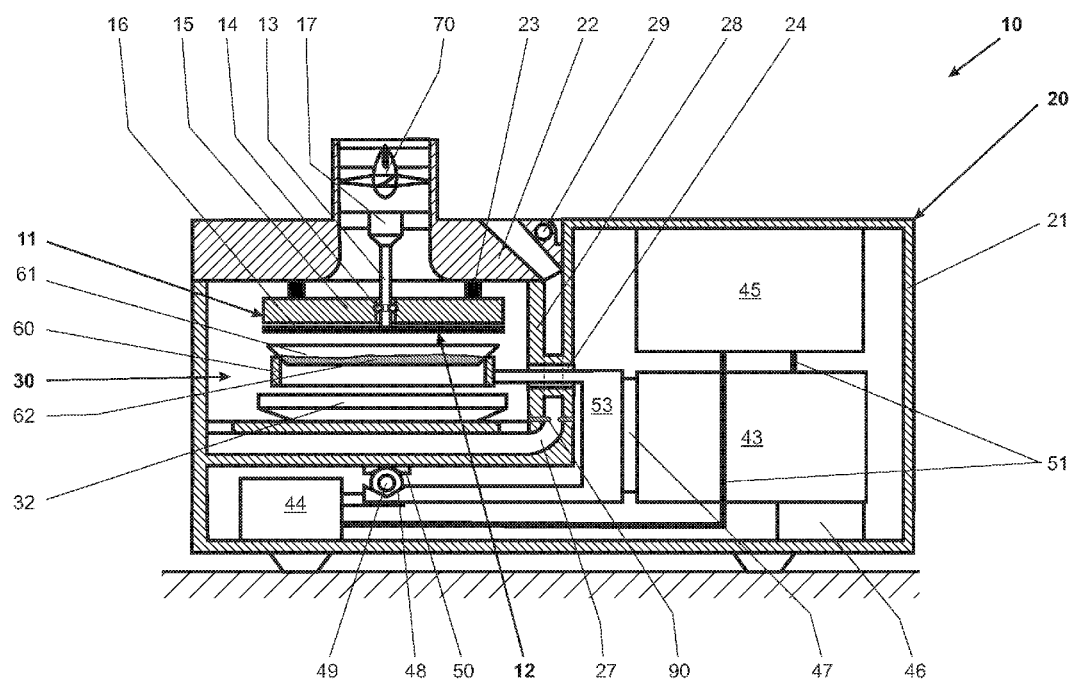
FIG. 1 is a sectional view of a measuring device with a housing in which the test compartment and the weighing cell are arranged side-by-side, and with the radiator installed in a lid which is hinged on the housing so that it can be raised or lowered on a substantially horizontal hinge axis, as well as a suction device incorporated in the lid and an insulating ventilation channel arranged between the weighing cell and the test compartment.

FIG. 1 shows a sectional view of a measuring instrument 10. The measuring instrument 10 has a housing 20 in which a test compartment 30 is arranged. The housing 20 is divided into a movable housing part 22 and a stationary housing part 21. Arranged in the stationary housing part 21 are a weighing cell 43, a calibration-weight-handling mechanism 44, and at least one electronic module 45, all of which are connected to each other by communicating means 51. The electronic module 45 contains at least one signal-processing module that is not shown in detail, and possibly also a control- and/or regulation module. The weighing cell 43 has at least a stationary portion 46 and a load-receiving portion 47. Known types of weighing cells are for example elastically deforming bodies carrying strain gauges, or weighing cells based on the principle of electromagnetic force compensation, or weighing cells with oscillating strings, capacitative weighing sensors and the like. The stationary portion 46 is rigidly connected to the stationary housing part 21. Arranged on the load-receiving portion 47 is a connecting member 53 which connects a sample receiver 60 to the load-receiving portion 47. As illustrated, a sample tray 61 with a sample 62 can be set on the sample receiver 60. With a suitable design of the sample receiver 60, one could of course also put the sample 62 directly on the sample receiver 60.

Further, a calibration weight receiver seat 48 is formed on the connecting member 53. A calibration weight 49 can be put on the weight receiver seat 48 by means of the calibration weight handling mechanism 44 actuated either by the user or under the control of the measuring instrument 10, in order to determine a correction value for the measuring signal based on the current operating condition of the measuring instrument 10. After the correction value has been determined, the calibration weight 49 is disconnected again from the calibration weight receiver seat 48 and held by the calibration weight handling mechanism 44 against a resting cradle 50 until the next calibration cycle takes place. Ideally, as a way to avoid eccentric load errors in the correction value, the mass center of the calibration weight 49 or—if applicable—the combined mass center of a plurality of calibration weights 49 lies close to an axis that passes through the center of gravity of the sample receiver 60 and/or of the sample tray 61 and/or the sample 62. The term "eccentric load error" (also referred to as corner load error) means the deviation that occurs in the weight measured by a weighing device for one and the same load when the latter is placed eccentrically on the sample receiver 60 in comparison to when it is put in a centered position.

As illustrated in FIG. 1, the movable housing part 22 is configured as a lid in which a radiation source 11 is arranged. A hinge 29 in the upper part of the housing 20 connects the movable housing part 22 to the stationary housing part 21, with the axle of the hinge 29 being arranged substantially horizontal. The movable housing part 22 forms the upper part of the test compartment 30. FIG. 1 shows the measuring instrument 10 in operating position, meaning the lid of the test compartment 30 is shown in the closed position.

The radiator 11 in the illustrated embodiment comprises in essence a disk 16 with the radiation-releasing surface 12, a shaft 13, a bearing 14 and a distributing body 15. The distributing body 15 in whose center the bearing 14 is formed is connected to the movable housing part 22 through support posts 23. Inside the distributing body 15 there can be heat radiators, heating foils, microwave generators, halogen- and quartz lamps arranged as radiation generators. The disk 16 consists preferably of a material with good thermal conductivity. Due to its thermal conductivity and density as well as the advantages of being easy to work with and resistant to corrosion, it is very advantageous to use aluminum and aluminum alloys. The aluminum parts are preferably given a coating, ideally black-anodized. However, the disk 16 can also be made of ceramic materials or glass. The bearing 14 holds the rotary shaft 13, whose axis of rotation is oriented in the direction of the load. The end of the shaft 13 that faces in the direction of the load is connected to the disk 16 with the radiation-releasing surface 12 whose shape and size essentially match the shape and size of the area filled by the sample 62. In the distributing body 15 radiation, essentially heat radiation, is generated which is transmitted to the disk 16 which, in turn releases the radiation to the sample 62 through the radiation-releasing surface that faces towards the sample. During the drying process, the disk 16 is set in rotation by a drive mechanism whose description follows. Due to the flat and planar configuration of the disk 16, its parallel alignment with the sample 62, its rotary movement, and the structure of its surface which is matched to the distance from the sample 62, the radiation emitted in the direction of the load by the radiation-releasing surface 12 can heat the sample 62 in a uniform manner.

Of course, designs are also possible in which the entire radiator 11 is rotatable. In this case, the radiation-releasing surface 12 is formed directly on the distributing body 15 and has the same properties and characteristics as described above. However, providing the radiator 11 with power becomes more involved with this design version. The supply with electrical power can be accomplished for example by way of a collector with carbon brushes.

A suction device 70 is incorporated above the radiation source 11 in the movable housing part 22. The suction device 70 consists of a static assembly in which a motor is incorporated, and of an axial rotor. In this embodiment, the shaft 13 of the preceding description is connected to a motor 17. Of course, the shaft 13 can also be connected directly or through a gearbox to the drive source of the suction device 70, in which case the separate motor 17 would be omitted. If a stream of the gaseous medium of sufficient volume and velocity flows through the test compartment 30 against the direction of the load, the disk 16 or the rotatably supported radiator 11 can also be equipped with blades similar to a turbine wheel of an axial turbine. In this case, the gas stream moving through the blades will set the disk 16 or the entire radiator 11 in rotation.

The lower part of the test compartment 30 is formed in the stationary housing part 21. The connecting member 53 which is mechanically connected to the weighing cell 43 protrudes likewise into the lower part of the test compartment 30, so that the sample receiver 60 which is connected to the connecting member 53 is arranged entirely in the test compartment 30. To provide thermal insulation, a wall 28 of the stationary housing part 21 between the weighing cell 43 and the test compartment 30 is configured at least in part as a double wall. With the double-walled configuration of the wall 28, a ventilation duct 27 is formed through which a gaseous medium can be directed into the test compartment 30. The medium flowing through the duct during the measuring process cools the wall 28, so that the heat radiated from the test compartment cannot penetrate into the part of the housing that contains the weighing cell 43. Of course, the gaseous medium conducted through the ventilation duct 27 does not necessarily have to be introduced into the test compartment. In this regard, it is also possible to use a simple ventilation duct of the kind disclosed in U.S. Pat. No. 6,920,781 B2.

There can further be a second radiator 32 arranged in the test compartment 30 below the sample receiver. As no moisture-saturated gas cushion can form in this area, the radiation-releasing surface of this second radiator 32 does not necessarily have to be set in rotation. Of course, this feature can still be adopted in the design, if it appears advisable in the interest of achieving a uniform radiation distribution.

There can further be various auxiliary devices arranged in the ventilation duct 27. For example, the gaseous medium can be ionized by means of an ionizer 90 in order to eliminate electrostatic charges inside the test compartment 30. To allow the connecting member to protrude into the test compartment, the wall 28 has a passage opening 24. This passage is configured as a closed tubular conduit, so that the medium streaming through the ventilation duct 27 cannot enter into the test compartment 30 through the passage 24 nor exert a force on the connecting member 53.

Figure 2A:
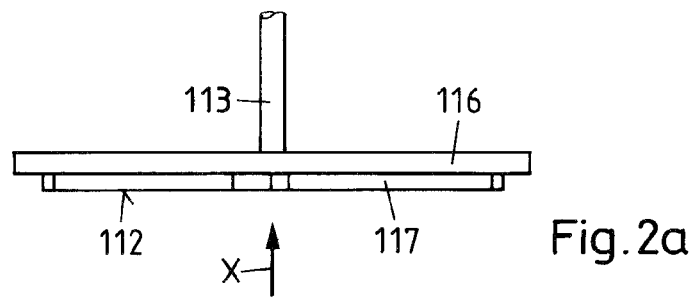
FIG. 2a is a sectional view of the radiation-releasing surface, shown as an enlarged detail of FIG. 1, and equipped with ridges.

The disk 116 that is shown in a sectional view in FIG. 2a is identical to the disk in FIG. 1, except for the ridges 117 that have been added to the radiation-releasing surface 112. In principle, there are no constraints imposed on the shape of these ridges. However, to meet the simultaneous requirements for the best possible removal of the moisture-enriched gaseous medium and the best possible uniformity of the radiation intensity, certain configurations are preferred, two of which are represented in FIGS. 2*b* and 2*c* in plan view as seen in the direction X indicated by the arrow in FIG. 2*a*.

Figure 2B:
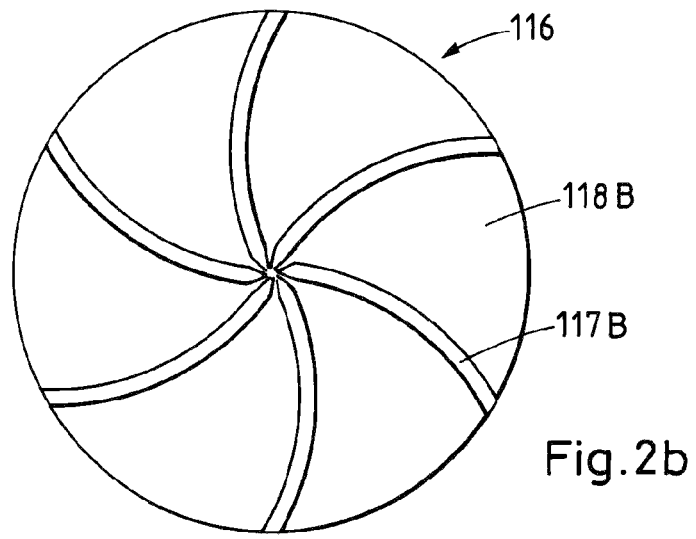
FIG. 2b is a plan view of the radiation-releasing surface of FIG. 2a, seen in the direction X that is indicated in FIG. 2a, with a first configuration of the ridges.

The disk 116 shown in FIG. 2*b* has narrow protruding ridges 117B of rectangular cross-section. These ridges 117B are curved in the radial direction. Accordingly the depressed areas 118B that are separated from each other by the ridges 117B are likewise curved in the radial direction. As is known from pumps and ventilation fans, the curvature makes it possible to choose the radial flow velocity as needed. As a result, stagnant accumulations of the gaseous medium between the ridges 117B, which could cause excessive turbulence between the sample and the radiation-releasing surface, can be prevented. Turbulences of this kind could critically influence the measuring result determined by the weighing cell. Of course, it is also possible that only a single ridge is formed on the radiation-releasing surface, with the single ridge being strongly curved in the radial direction so that it forms a spiral on the radiation-releasing surface.

Figure 2C:
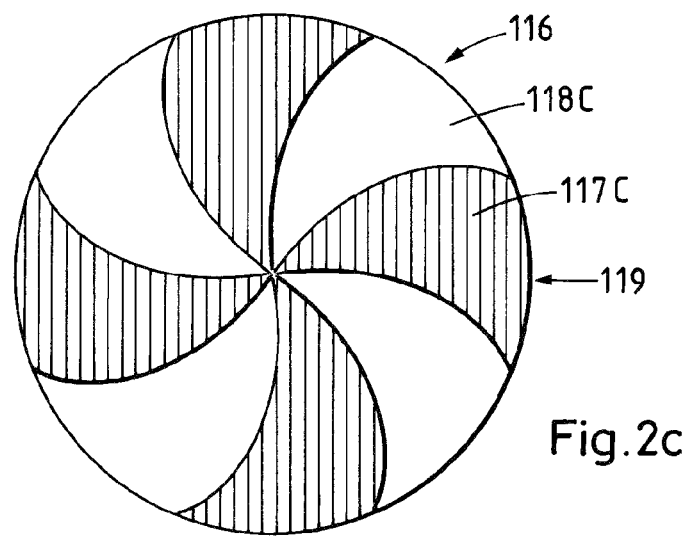
FIG. 2c is a plan view of the radiation-releasing surface of FIG. 2a, seen in the direction X that is indicated in FIG. 2a, with a second configuration of the ridges.

The disk 116 shown in FIG. 2*c* is likewise equipped with protruding ridges 117*c*, which are shaded in the drawing for better clarity. However, unlike the ridges in FIG. 2*b*, the width of the ridges 117*c* gets continuously larger towards the border 119 of the disk 116, so that the raised surfaces of the ridges 117C are equal to the depressed surfaces 118C which are formed between the ridges 117C. This results in a further improvement in the uniformity of the radiation intensity in comparison to the embodiment shown in FIG. 2*b*. The ridges 117C and depressions 118C are likewise curved in the radial direction as described in detail for FIG. 2*b*.

Figure 3:
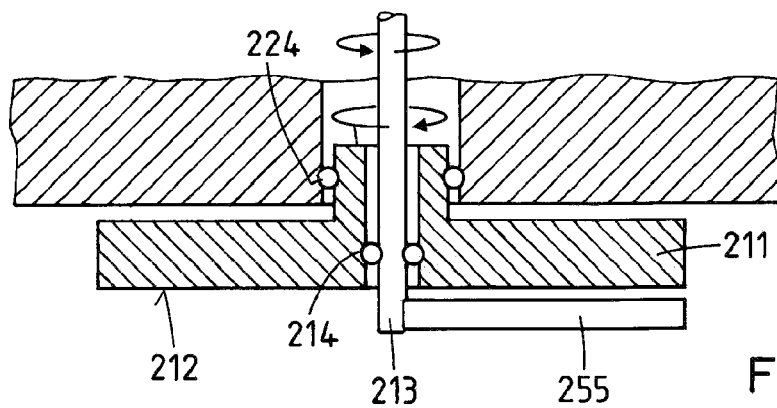
FIG. 3 is a sectional view of a rotatably supported radiator, with a central opening through which a shaft passes at whose end a dynamic displacement body is arranged.

A further embodiment is illustrated schematically in FIG. 3. Shown in a cross-sectional view, a radiator 211 which is rotatably supported by a bearing 224 mounted in a fixed position of the housing has in its center a bore hole with a bearing 214 holding a shaft 213 that passes through the bore hole and carries at its end a wiper blade as a dynamic displacement body 255. A radiation-releasing surface 212 is formed on the radiator 211. As illustrated in FIG. 1, in place of a rotatably supported radiator 211 it is also possible to use a radiator in which the radiation-releasing surface is designed to be rotatable. When in operation, the radiator 211 spins with the opposite sense of rotation of the shaft 213 in order to achieve a high removal rate with the slowest possible rates of rotation. The shaft 213 as well as the radiator 211 can each be coupled to its own drive source which is not shown in FIG. 3. However, other versions of a drive mechanism are also conceivable where the radiator 211 is coupled to the shaft 213 through a gear stage.

Figure 4:
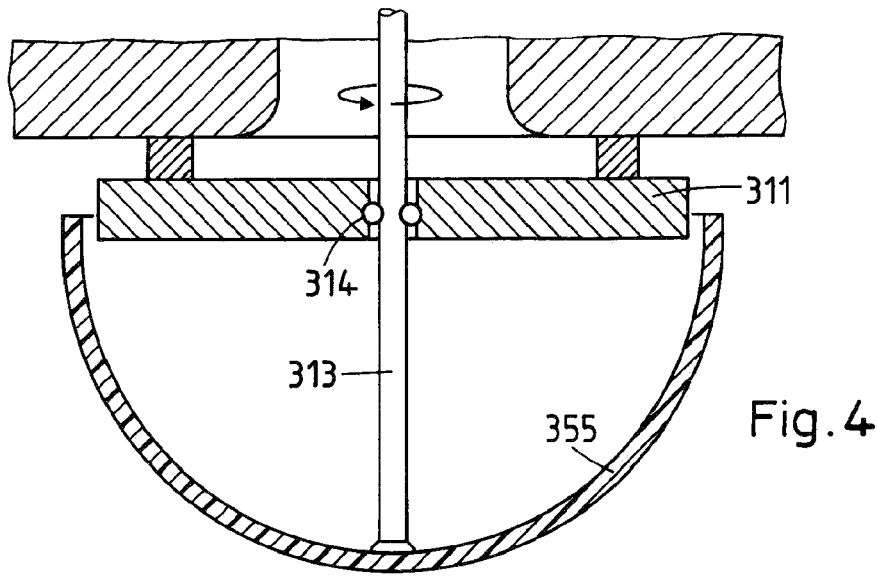
FIG. 4 is a sectional view of a radiator that is mounted in a fixed position in the housing, with a central opening through which a shaft passes at whose end a dynamic displacement body of radiation-transmitting material is arranged.

FIG. 4 shows a sectional view of a radiator 311 that is mounted in a fixed position on the housing and has a bore hole 314 at its center where a shaft 313 is rotatably constrained by a bearing. Arranged at the end of the shaft 313 is a dynamic displacement body 355 in the form of a bonnet of a radiation-transmitting material. The dynamic displacement body 355 in this embodiment has the shape of a hemisphere, but other rotationally symmetric shapes can also be used, such as cones, stepped cones and the like. The dynamic displacement body 355 can have ridges, grooves or depressions arranged on the surface that faces away from the radiator 311.

Figure 5:
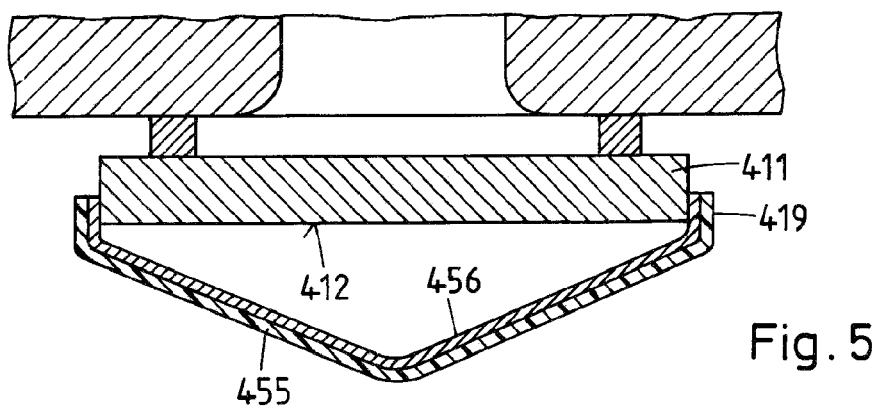
FIG. 5 is a sectional view of a radiator that is mounted in a fixed position in the housing, with a cone-shaped static displacement body of radiation-transmitting material arranged over the radiation-releasing surface and solidly connected to the radiator, wherein the displacement body has a partially absorbent layer on its inside surface.

FIG. 5 shows a sectional view of a radiator 411 that is mounted in a fixed position on the housing. Arranged over the radiation-releasing surface 412 of the radiator 411 is a bonnet of radiation-transmitting material, which works as a static displacement body 455 and has a fixed connection to the radiator 411. As a result of the heat radiation, the gaseous medium which is enriched with moisture from the sample rises towards the static displacement body 455, whose shape directs or pushes the gaseous medium towards the border 419 of the radiator 411. The static displacement body 455 has a partially absorbent coating 456 on the inside surface that faces towards the radiator 411. This coating 456 absorbs a part of the radiation emitted by the radiator 411 and thereby heats the static displacement body 455. This avoids the problem that the moisture escaping from the sample could condense on a cold displacement body 455. Of course, this embodiment can likewise be supplemented as shown in FIG. 3 with a dynamic displacement body that is matched to the contour of the static displacement body.

Figure 6:
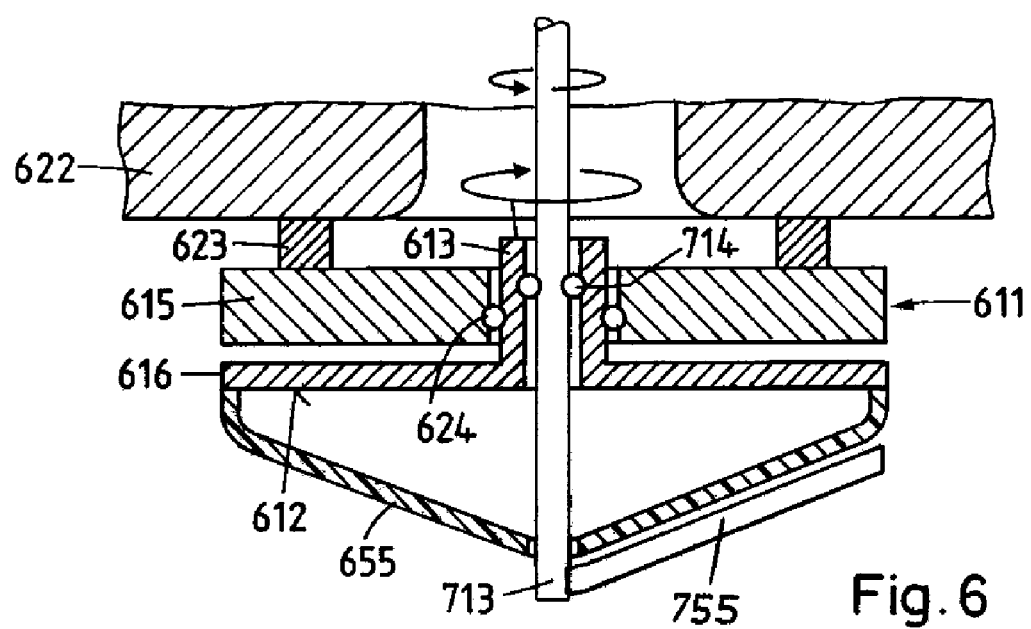
FIG. 6 is a sectional view of a rotatably supported radiator in a sectional view with a first displacement body and with an opening at the center through which a shaft passes at whose end a second dynamic displacement body is arranged.

A possible way of combining the embodiments of the foregoing description is illustrated in FIG. 6. The radiator 611 is largely identical to the radiator in FIG. 1, comprising in essence a disk 616 with the radiation-releasing surface 612, a hollow shaft 613, a second bearing 624, and a distributing body 615. The distributing body 615 at whose center the second bearing 624 is formed is connected through support posts 623 to the housing 620 of the measuring instrument. A first dynamic displacement body 655 is connected to the rotatable disk 616. The radiation-releasing surface 612 and the first dynamic displacement body 655 have a central passage opening. Arranged in the hollow shaft 613 is a bearing 714 which holds a shaft 713. The hollow shaft 613 as well as the shaft 713 are constrained to rotate about an axis parallel to the load direction. Connected to the end of the shaft that faces towards the sample is a second dynamic displacement body 755. The radiation-releasing surface 612 with the first dynamic displacement body 655 connected to it turns with the opposite sense of rotation as the shaft 713 that drives the second dynamic displacement body 755.

The embodiments presented here show measuring instruments for the gravimetric determination of moisture content with different properties and features. In the interest of clarity, the different properties and features have been shown in different embodiments, but it is also possible to realize a combination of the proposed features and properties in a measuring instrument. Furthermore, solutions in which the shaft does not pass through an opening in the radiator but runs outside of the radiator are likewise within the intended scope. Nor is the invention limited to configurations with only one shaft. Furthermore, a continuous rotary movement is not a necessary condition for performing the function; it is also possible and within the intended scope that the shaft and/or the radiation-releasing surface oscillates back and forth. The scope of the invention is not limited to the configuration of the weighing cell and the housing as shown in FIG. 1, but can be used in all known measuring instruments that have radiators arranged above the sample.

What is claimed is:

1. A measuring instrument for gravimetric moisture determination of a sample, comprising:
    a weighing cell; and
    a sample receiver, adapted for placement of the sample thereon and removal of the sample therefrom and for connection to the weighing cell;
    at least one radiator, arranged above the sample in relation to a load direction of the weighing cell and spanning the area of the sample, the at least one radiator having a radiation-releasing surface directed at the sample and providing a radiation of uniform intensity that substantially covers the entire surface of the sample, and
    a means for removing moisture generated during operation from a space between the sample and the radiation-releasing surface.

2. The measuring instrument of claim 1, wherein:
the radiation-releasing surface is arranged to be rotatable relative to the sample to serve as the moisture-removing means.

3. The measuring instrument of claim 2, wherein:
the radiation-releasing surface has a surface roughness of at least 0.0001 mm.

4. The measuring instrument of claim 3, wherein:
the radiation-releasing surface has at least one ridge, groove, channel or depression.

5. The measuring instrument of claim 4, wherein:
the radiation-releasing surface has both ridges and depressions and the raised surfaces of the ridges cover areas of the same shape and size as the depressions.

6. The measuring instrument of claim 1, wherein:
the moisture-removing means comprises a static displacement body, arranged between the sample and the at least one radiator and comprising a radiation-transmitting material.

7. The measuring instrument of claim 6, wherein:
the static displacement body is provided at least in part with a partially absorbent member.

8. The measuring instrument of claim 6, wherein:
the static displacement body is connected to at least one of the radiation-releasing surface and a housing part of the measuring instrument.

9. The measuring instrument of claim 6, wherein:
the static displacement body is a cone-shaped or spherically shaped bonnet, a curved plate, or a planar plate which is arranged at an angle $\alpha$ relative to the direction of the load, wherein the angle $\alpha$ is in the range $0°<\alpha<90°$.

10. The measuring instrument of claim 6, further comprising:
a central bearing;
a shaft that passes through the bearing, the shaft being constrained by the bearing to rotate or swivel about an axis parallel to the load direction, and
a dynamic displacement body is connected to an end of the shaft that faces towards the sample;
wherein the central bearing, the shaft and the dynamic displacement body are associated with at least one of: the radiation-releasing surface and the static displacement body.

11. The measuring instrument of claim 10, wherein:
the dynamic displacement body comprises a wiper blade or a scoop that curves in the radial and/or axial direction relative to the axis of the shaft.

12. The measuring instrument of claim 10, wherein:
a releasable fastener element connects the shaft to at least one of: the dynamic displacement body and the radiation-releasing surface.

13. The measuring instrument of claim 10, wherein:
the radiation-releasing surface spins in a first direction and the shaft spins in an opposite second direction.

14. The measuring instrument of claim 10, wherein:
the dynamic displacement body comprises a radiation-transmitting material and is a cone or a spherically shaped bonnet.

15. The measuring instrument of claim 13, wherein:
the dynamic displacement body has at least one of: a partially absorbent member and at least one ridge, groove, channel or depression.

16. The measuring instrument of claim 1, wherein:
the moisture removing means comprises:
a first dynamic displacement body connected to at least one of the radiator or the radiation-releasing surface thereof, the first dynamic displacement body arranged to rotate relative to the sample;
a bearing; and
a shaft that passes through the bearing and is constrained thereby to rotate or swivel about an axis parallel to the direction of the load; and
a second dynamic displacement body, connected to an end of the shaft that faces towards the sample,
wherein the first and second dynamic displacement bodies rotate in opposite directions relative to the axis of the shaft.

17. The measuring instrument of claim 16, wherein:
the respective areas covered by geometrically projecting the radiation-releasing surface and the sample into a plane that is orthogonal to the load direction have substantially identical size and shape.

18. The measuring instrument of claim 16, wherein:
the radiation-releasing surface is substantially flat and planar and is arranged parallel to the surface of the sample.

19. The measuring instrument of claim 18, wherein:
the displacement body covers the entire radiation-releasing surface.

20. The measuring instrument of claim 1, wherein:
a releasable fastener element connects the static displacement body to at least one of: the radiation source and a housing of the measuring instrument.

21. The measuring instrument of claim 1, wherein:
the radiation-releasing surface has a central bearing and a shaft that passes through the bearing, the shaft being constrained by the bearing to rotate or swivel about an axis parallel to the load direction, and
at least one dynamic displacement body is connected to an end of the shaft that faces towards the sample.

22. The measuring instrument of claim 21, wherein:
the dynamic displacement body comprises a wiper blade or a scoop that curves in the radial and/or axial direction relative to the axis of the shaft.

23. The measuring instrument of claim 21, wherein:
the dynamic displacement body comprises a radiation-transmitting material and is a cone or a spherically shaped bonnet.

24. The measuring instrument of claim 21, wherein:
the radiation-releasing surface spins in a first direction and the shaft spins in an opposite second direction.

25. The measuring instrument of claim 24, wherein:
the dynamic displacement body has at least one of: a partially absorbent member and at least one ridge, groove, channel or depression.

26. The measuring instrument of claim 1, wherein:
the respective areas covered by geometrically projecting the radiation-releasing surface and the sample into a plane that is orthogonal to the load direction have substantially identical size and shape.

27. The measuring instrument of claim 1, wherein:
the radiation-releasing surface is substantially flat and planar and is arranged parallel to the surface of the sample.

* * * * *

UNITED STATES PATENT AND TRADEMARK OFFICE
CERTIFICATE OF CORRECTION

PATENT NO. : 7,591,169 B2
APPLICATION NO. : 11/769415
DATED : September 22, 2009
INVENTOR(S) : Lüchinger Page 1 of 1

It is certified that error appears in the above-identified patent and that said Letters Patent is hereby corrected as shown below:

In column 4, line 54, please delete "angle a" and insert -- angle α --.

Signed and Sealed this

Twentieth Day of October, 2009

David J. Kappos
*Director of the United States Patent and Trademark Office*